United States Patent [19]

Schwarzmann et al.

[11] 4,120,979
[45] Oct. 17, 1978

[54] ALKYLATED POLYAMINES, THEIR PREPARATION AND USE AS MICROBIOCIDES

[75] Inventors: Günter Schwarzmann; Ulrich Holtschmidt; Günter Bertelmann, all of Essen, Germany

[73] Assignee: Th. Goldschmidt AG, Germany

[21] Appl. No.: 830,772

[22] Filed: Sep. 6, 1977

[30] Foreign Application Priority Data

Sep. 17, 1976 [DE] Fed. Rep. of Germany ....... 2641836

[51] Int. Cl.$^2$ .......................... A01N 9/20; C07C 87/14; C07C 87/20
[52] U.S. Cl. .................................. 424/325; 260/583 P
[58] Field of Search ...................... 424/325; 260/583 P

[56] References Cited

U.S. PATENT DOCUMENTS

| | | | |
|---|---|---|---|
| 2,246,524 | 6/1941 | Kyrides | 260/583 P |
| 4,004,030 | 1/1977 | Schwarzmann et al. | 424/325 |

OTHER PUBLICATIONS

Chemical Abstracts, vol. 77 (1972), p. 29820t.

*Primary Examiner*—V. D. Turner
*Attorney, Agent, or Firm*—James E. Bryan

[57] ABSTRACT

This invention relates to a compound or mixture of compounds having the general formula

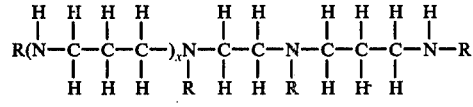

in which R is hydrogen or an alkyl group containing 8 to 18 carbon atoms, at least one R being alkyl, and $x$ is 0 or 1. The invention also relates to a process for making the novel compound or mixture thereof, a process for killing microbes using the novel compound or mixture thereof, and a microbiocidal composition using the novel compound or mixture thereof.

9 Claims, No Drawings

ALKYLATED POLYAMINES, THEIR PREPARATION AND USE AS MICROBIOCIDES

The present invention is in the same art as German Pats. Nos. 2,049,399, and 2,113,208.

German Pat. No. 2,049,399 relates to a biocidal preparation containing effective amounts of a synergistic mixture of compounds of the general formula I

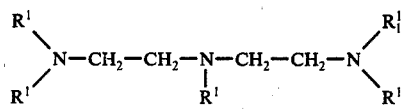

where $R^1$ denotes hydrogen or $C_8H_{17}$, but where two of $R^1$ are $C_8H_{17}$, and of compounds of the formula II

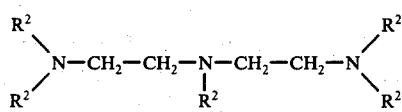

where $R^2$ denotes hydrogen or $C_8H_{17}$, but where at least three of $R^2$ are $C_8H_{17}$, the weight ratio of the compounds of formula I to those of formula II being 50 : 50 to 90 : 10.

German Pat. No. 2,113,208 relates to compounds of the general formula

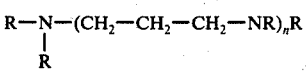

where R is hydrogen or $C_8H_{17}$, but where at least two of R are $C_8H_{17}$, and where n is either 1 or 2, this patent relating to the preparation and use of the compounds as disinfectants, preservatives and sanitary cleansing agents.

The present invention relates to producing microbiocidal compounds with an effectiveness superior to that of these known compounds.

Surprisingly it was found that a very closely related group of alkylated polyamines offers especially pronounced sporicidal effects in addition to good bactericidal and fungicidal properties.

These new compounds involve compounds or mixtures of compounds of the general formula

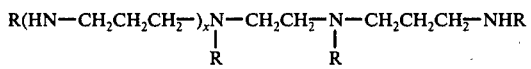

where R is hydrogen or an alkyl group with 8 to 18 carbon atoms, but where at least one R is an alkyl group and where x is 0 or 1.

Straight-chain as well as branched-chain alkyl groups may be selected as alkyl groups with 8 to 18 carbon atoms. However, the straight chain alkyl groups are preferred, and, of these, those with even numbers of carbon atoms.

The term "mixture of compounds" denotes both a mixture of polyamines substituted at various nitrogen atoms and a mixture of compounds for which x is 1 or 0.

The compounds or mixtures of compounds of the invention may be prepared in known manner by reacting an amine or a mixture of amines of the formula

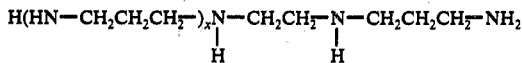

with an alkyl halogen containing from 8 to 18 carbon atoms in a molar ratio from 4 : 1 to 1 : 6 in the presence of acid acceptors and at temperatures from 80° to 200° C. and thereupon removing the non-converted reactants, if appropriate by distillation. Suitable acid acceptors are, for instance, NaOH, KOH, Ca(OH)$_2$, Na$_2$CO$_3$, NaHCO$_3$ or the polyamines present in excess.

The preferred conversion temperature is in the range of 100° to 150° C.

The compounds or mixtures of compounds or the excess polyamines of the invention may be isolated from the reaction mixture by fractional distillation, depending upon the boiling point.

The compounds of the invention may be used as such, generally in the form of their salts, for instance as acetates, lactates, citrates, gluconates, hydrochlorides or phosphates, or in the form of liquid, pasty or solid preparations.

Appropriate solvents for the compounds of the invention are, for instance, water, methanol, ethanol, propanol, methylglycol, ethylglycol, propylene glycol, dimethyl sulfoxide and dimethyl formamide.

Additionally, dispersing agents such as non-ionic surfactants, for instance ethoxylation products of lauryl alcohol, tridecyl alcohol, isooctyl phenol and nonyl phenol, copolymerizates of ethylene oxide and propylene oxide, inert fillers such as highly dispersed silica, aluminum oxide, zinc sulfide, titanium dioxide as well as urea, cane sugar and cellulose, thickening agents such as methyl cellulose, hydroxyethyl cellulose and carboxy methyl cellulose, polyvinyl pyrrolidone, and polyvinyl alcohol, also dyestuffs and odorants, may be present in preparations containing the compounds of the invention.

In addition to good bactericidal and fungicidal properties, the compounds or mixtures of compounds of the invention also exhibit superlative sporicidal qualities. They are therefore particularly well suited as disinfectants in hospitals, food-processing plants, and animal fattening and raising operations. It furthermore is surprising that the polyamines containing mixed groups of ethylene and propylene are superior to the individual polyamines containing propylene or ethylene groups.

The following examples show the preparation of the compound or mixtures of compounds of the invention and their microbiocidal, and particularly sporicidal effectiveness, and they compare their effectiveness with the sporicidal one of the compounds of German Pats. Nos. 2,049,399, and 2,113,208.

The bacteriological experiments were carried out according to the guidelines of the German Society of Sanitation and Microbiology (Deutschen Gesellschaft für Hygiene und Mikrobiologie), except that in lieu of distilled water for making the individual dilution stages, water of 15° d.H. was used because of greater practically.

Testing of the sporicidal properties was carried out in such a manner that spores from a 10-day old culture were liberally washed and twice heated to 80° C. for 1 to 2 hours to rid them of vegetative germs. Otherwise the test was carried out similarly to the suspension test of the above guidelines.

(a) Derivatives of 3-(2-aminoethyl-)aminopropylamine

H₂N—CH₂CH₂—NH—CH₂CH₂CH₂—NH₂

EXAMPLE 1

Conversion product of 3-(2-aminoethyl)-aminopropylamine with n-octylchloride in a molar ratio of 1 : 3.

1 mole of amine is heated together with 1.6 moles of sodium hydroxide and 15 ml of water to 120° C. 3 moles of n-octylchloride are added to this mixture, while stirring, and reaction is allowed to continue for 12 hours at 130° C. Thereupon, the inorganic residue is removed hot by filtration. The filtrate of 426 g is used for preparing microbiocidal substances.

Analyses: Computed: % by weight, C = 76.7; H = 14.0; N = 9.3. Measured: % by weight: C = 76.5; H = 14.1; N = 9.1.

10 parts of reaction product are stirred while being heated together with 8 parts by weight of an adduct of 10 moles of ethylene oxide added to 1 mole of i-tridecyl alcohol, with 10 parts by weight of acetic acid and 72 parts by weight of water until a clear solution is obtained which can be mixed with water in any proportion. The pH value of the preparation was adjusted by means of acetic acid to 7.05.

| Test Strain | Preparation of Example 1 Concentration of effective substance % ES | Time to become effective/min. 1 | 2 | 5 | 10 | 20 | 30 |
|---|---|---|---|---|---|---|---|
| S. aureus | 0.1 | − | − | − | − | − | − |
| | 0.05 | − | − | − | − | − | − |
| | 0.01 | + | − | − | − | − | − |
| | 0.005 | + | + | − | − | − | − |
| | 0.001 | + | + | + | − | − | − |
| E. Coli | 0.1 | − | − | − | − | − | − |
| | 0.05 | − | − | − | − | − | − |
| | 0.01 | − | − | − | − | − | − |
| | 0.005 | + | − | − | − | − | − |
| | 0.001 | + | + | + | + | + | + |
| P. vulgaris | 0.1 | − | − | − | − | − | − |
| | 0.05 | + | + | − | − | − | − |
| | 0.01 | + | + | + | + | + | + |
| | 0.005 | + | + | + | + | + | + |
| | 0.001 | + | + | + | + | + | + |
| P. aeruginosa | 0.1 | − | − | − | − | − | − |
| | 0.05 | − | − | − | − | − | − |
| | 0.01 | + | + | + | + | + | + |
| | 0.005 | + | + | + | + | + | + |
| | 0.001 | + | + | + | + | + | + |
| Candida Albicans | 0.1 | − | − | − | − | − | − |
| | 0.05 | − | − | − | − | − | − |
| | 0.01 | − | − | − | − | − | − |
| | 0.005 | + | + | − | − | − | − |
| | 0.001 | + | + | − | − | − | − |
| Hansenual anomala | 0.1 | − | − | − | − | − | − |
| | 0.05 | − | − | − | − | − | − |
| | 0.01 | + | + | − | − | − | − |
| | 0.005 | + | + | − | − | − | − |
| | 0.001 | + | + | + | + | + | − |
| Geotrichum candidum | 0.1 | − | − | − | − | − | − |
| | 0.05 | − | − | − | − | − | − |
| | 0.01 | − | − | − | − | − | − |
| | 0.005 | − | − | − | − | − | − |
| | 0.001 | + | + | − | − | − | − |
| Pencillium expansum | 0.1 | − | − | − | − | − | − |
| | 0.05 | − | − | − | − | − | − |
| | 0.01 | + | + | − | − | − | − |
| | 0.005 | + | + | − | − | − | − |
| | 0.001 | + | + | + | + | + | − |
| Trichophyton mentagrophytes | 0.1 | − | − | − | − | − | − |
| | 0.05 | − | − | − | − | − | − |
| | 0.01 | − | − | − | − | − | − |
| | 0.005 | − | − | − | − | − | − |
| | 0.001 | + | + | + | − | − | − |
| Mikrosporum gypseum | 0.1 | − | − | − | − | − | − |
| | 0.05 | − | − | − | − | − | − |
| | 0.01 | + | − | − | − | − | − |
| B. Cereus (spores) | 0.005 | + | − | − | − | − | − |
| | 0.001 | + | + | + | + | − | − |
| | 0.1 | − | − | − | − | − | − |
| | 0.05 | − | − | − | − | − | − |
| | 0.01 | + | + | + | + | + | − |
| | 0.005 | + | + | + | + | + | + |
| | 0.001 | + | + | + | + | + | + |
| B. Subtilis (spores) | 0.1 | − | − | − | − | − | − |
| | 0.05 | − | − | − | − | − | − |
| | 0.01 | + | + | + | + | + | + |
| | 0.005 | + | + | + | + | + | + |
| | 0.001 | + | + | + | + | + | + |

ES = Effective Substance;
− indicates no germ growth;
+ indicates germ growth.

EXAMPLE 2

Reaction product of 3-(2-aminoethyl)-aminopropylamine with n-decylchloride in a molar ratio of 1 : 1.

8 moles of amine are heated together with 50 ml of water and 12.8 moles of sodium hydroxide to a temperature of 120° C. 8 moles of n-decyl chloride are added to this mixture, while stirring, and the reaction is allowed to continue for 10 hours. Thereupon, the inorganic residue is removed hot by filtration and the filtrate is freed from non-converted initial amine by distillation. The remaining alkyl polyamine mixture is used for preparing microbiocidal substances. Yield = 809 g.

10 parts by weight of the reaction product are homogenized with 10 parts by weight of an adduct of 10 moles of ethylene oxide on 1 mole of i-tridecyl alcohol, 10 parts by weight of acetic acid and 70 parts by weight of water while stirring and heating about 45° C. until a clear yellow solution is obtained which may be mixed with water in any proportion. The pH value of the preparation was adjusted to 7.0 with acetic acid.

| Test Strain | Preparation of Example 2 Concentration of effective substance % ES | Time to become effective/min. 1 | 2 | 5 | 10 | 20 | 30 |
|---|---|---|---|---|---|---|---|
| S. aureus | 0.1 | − | − | − | − | − | − |
| | 0.05 | − | − | − | − | − | − |
| | 0.01 | − | − | − | − | − | − |
| | 0.005 | − | − | − | − | − | − |
| | 0.001 | + | + | − | − | − | − |
| E. coli | 0.1 | − | − | − | − | − | − |
| | 0.05 | − | − | − | − | − | − |
| | 0.01 | − | − | − | − | − | − |
| | 0.005 | − | − | − | − | − | − |
| | 0.001 | − | − | − | − | − | − |
| P. vulgaris | 0.1 | − | − | − | − | − | − |
| | 0.05 | − | − | − | − | − | − |
| | 0.01 | − | − | − | − | − | − |
| | 0.005 | + | + | − | − | − | − |
| | 0.001 | + | + | + | + | + | + |
| P. aeruginosa | 0.1 | − | − | − | − | − | − |
| | 0.05 | − | − | − | − | − | − |
| | 0.01 | − | − | − | − | − | − |
| | 0.005 | − | − | − | − | − | − |
| | 0.001 | + | + | + | + | + | + |
| B. cereus (spores) | 0.1 | − | − | − | − | − | − |
| | 0.5 | − | − | − | − | − | − |
| | 0.01 | + | + | + | + | + | − |
| | 0.005 | + | + | + | + | + | + |
| | 0.001 | + | + | + | + | + | + |
| B. subtilis (spores) | 0.1 | − | − | − | − | − | − |
| | 0.05 | − | − | − | − | − | − |
| | 0.01 | + | + | + | + | + | + |
| | 0.005 | + | + | + | + | + | + |
| | 0.001 | + | + | + | + | + | + |

(a) Derivatives of
N,N'-bis-(3-aminopropyl-)ethylenediamine $H_2N-CH_2CH_2CH_2-NH-CH_2CH_2NH-CH_2CH_2CH_2-NH_2$

EXAMPLE 3

Reaction product of N,N'-bis-(3-aminopropyl)-ethylenediamine with n-octylchloride in a molar ratio of 1 : 3.

1 mole of N,N'-bis-(3-aminopropyl)-ethylenediamine is heated together with 4.8 moles of sodium hydroxide to 120° C. 3 moles of n-octylchloride are added, while stirring, and the reaction is allowed to proceed for 10 hours at 135°–140° C. Thereupon, the reaction mixture is filtered hot, the inorganic residue is eliminated and the filtrate of 506 g is used for preparing the microbiocidal substances.

Analyses (computed for tri-n-octyl-N,N'-bis-(3-aminopropyl)-ethylenediamine): Computed: in % by weight: C = 75.2; H = 13.8; N = 11.0. Measured: in % by weight: C = 74.9; H = 13.6; N = 10.8.

10 parts by weight of the reaction product together with 10 parts by weight of an adduct of 10 moles of ethylene oxide to 1 mole of 1-tridecyl alcohol, with 70 parts by weight of water and 10 parts by weight of acetic acid are stirred until a clear yellow solution is obtained which can be mixed with water in any proportion. The pH of the preparation is adjusted to 6.85 by means of acetic acid.

| Test Strain | Preparation of Example 3 Concentration of effective substance % ES | Time to become effective/min. 1 | 2 | 5 | 10 | 20 | 30 |
|---|---|---|---|---|---|---|---|
| S. aureus | 0.1 | − | − | − | − | − | − |
|  | 0.05 | − | − | − | − | − | − |
|  | 0.01 | − | − | − | − | − | − |
|  | 0.005 | + | − | − | − | − | − |
|  | 0.001 | + | + | + | − | − | − |
| E. coli | 0.1 | − | − | − | − | − | − |
|  | 0.05 | − | − | − | − | − | − |
|  | 0.01 | − | − | − | − | − | − |
|  | 0.005 | − | − | − | − | − | − |
|  | 0.001 | + | + | + | − | − | − |
| P. vulgaris | 0.1 | − | − | − | − | − | − |
|  | 0.05 | + | + | − | − | − | − |
|  | 0.01 | + | + | + | + | + | − |
|  | 0.005 | + | + | + | + | + | + |
|  | 0.001 | + | + | + | + | + | + |
| P. aeruginosa | 0.1 | − | − | − | − | − | − |
|  | 0.05 | − | − | − | − | − | − |
|  | 0.01 | − | − | − | − | − | − |
|  | 0.005 | + | + | + | − | − | − |
|  | 0.001 | + | + | + | + | + | + |
| Candida albicans | 0.1 | − | − | − | − | − | − |
|  | 0.05 | − | − | − | − | − | − |
|  | 0.01 | − | − | − | − | − | − |
|  | 0.005 | − | − | − | − | − | − |
|  | 0.001 | + | + | − | − | − | − |
| Hansenula anomala | 0.1 | − | − | − | − | − | − |
|  | 0.05 | − | − | − | − | − | − |
|  | 0.01 | − | − | − | − | − | − |
|  | 0.005 | + | + | − | − | − | − |
|  | 0.001 | + | + | + | − | − | − |
| Geotrichum candidum | 0.1 | − | − | − | − | − | − |
|  | 0.05 | − | − | − | − | − | − |
|  | 0.01 | − | − | − | − | − | − |
|  | 0.005 | − | − | − | − | − | − |
|  | 0.001 | + | − | − | − | − | − |
| Penicilliim expansum | 0.1 | − | − | − | − | − | − |
|  | 0.05 | − | − | − | − | − | − |
|  | 0.01 | + | + | + | − | − | − |
|  | 0.005 | + | + | + | − | − | − |
|  | 0.001 | + | + | + | + | + | − |
| Trichophyton mentagrophytes | 0.1 | − | − | − | − | − | − |
|  | 0.05 | − | − | − | − | − | − |
|  | 0.01 | − | − | − | − | − | − |
|  | 0.005 | + | − | − | − | − | − |
|  | 0.001 | + | + | + | − | − | − |

-continued

| Test Strain | Preparation of Example 3 Concentration of effective substance % ES | Time to become effective/min. 1 | 2 | 5 | 10 | 20 | 30 |
|---|---|---|---|---|---|---|---|
| Mikrosporum gypseum | 0.1 | − | − | − | − | − | − |
|  | 0.05 | − | − | − | − | − | − |
|  | 0.01 | + | − | − | − | − | − |
|  | 0.005 | + | − | − | − | − | − |
|  | 0.001 | + | + | − | − | − | − |
| B. cereus (spores) | 0.1 | − | − | − | − | − | − |
|  | 0.05 | − | − | − | − | − | − |
|  | 0.01 | + | + | + | + | + | + |
|  | 0.005 | + | + | + | + | + | + |
|  | 0.001 | + | + | + | + | + | + |
| B. subtilis (spores) | 0.1 | − | − | − | − | − | − |
|  | 0.05 | − | − | − | − | − | − |
|  | 0.01 | + | + | + | + | + | + |
|  | 0.005 | + | + | + | + | + | + |
|  | 0.001 | + | + | + | + | + | + |

EXAMPLE 4

Reaction product of N,N'-bis-(3-aminopropyl)-ethylenediamine with lauryl chloride in a molar ratio of 4 : 1.

12 moles of N,N'-bis-(3-aminopropyl)-ethylenediamine are heated together with 35 ml of water to 120° C. 3 moles of lauryl chloride are added within 1 hour, while stirring, and the mixture is allowed to react for 12 hours at 135° C. Thereupon 4.8 moles of sodium hydroxide are added in small quantities. After a further 10 minutes the inorganic residue is removed hot by filtration and the filtrate is fractionally distilled. Following a first running of non-converted amine, 724 g of N-(3-laurylaminopropyl)-N'-(3-aminopropyl)ethylenediamine are obtained at 190°–193° C. and 0.05 torr.

Analyses: Computed: in % by weight: C = 70.1; H = 13.5; N = 16.4. Measured: in % by weight: C = 70.0; H = 13.4; N = 16.2.

10 parts by weight of the reaction product are homogenized while stirring together with 10 parts by weight of an adduct of 10 moles of ethylene oxide to 1 mole of i-tridecyl alcohol and with 5 parts by weight of acetic acid. The pH value of the preparation was adjusted to 8.25 using acetic acid.

| Test Strain | Preparation of Example 4 Concentration of effective substance - % ES | Time to become effective/min. 1 | 2 | 5 | 10 | 20 | 30 |
|---|---|---|---|---|---|---|---|
| S. aureus | 0.1 | − | − | − | − | − | − |
|  | 0.05 | − | − | − | − | − | − |
|  | 0.01 | + | + | + | − | − | − |
|  | 0.005 | + | + | + | − | − | − |
|  | 0.001 | + | + | + | + | + | − |
| E. coli | 0.1 | − | − | − | − | − | − |
|  | 0.05 | − | − | − | − | − | − |
|  | 0.01 | + | + | + | + | − | − |
|  | 0.005 | + | + | + | + | + | − |
|  | 0.001 | + | + | + | + | + | − |
| P. vulgaris | 0.1 | + | − | − | − | − | − |
|  | 0.05 | + | + | − | − | − | − |
|  | 0.01 | + | + | + | + | − | − |
|  | 0.005 | + | + | + | + | + | − |
|  | 0.001 | + | + | + | + | + | + |
| P. aeruginosa | 0.1 | − | − | − | − | − | − |
|  | 0.5 | − | − | − | − | − | − |
|  | 0.01 | + | + | − | − | − | − |
|  | 0.005 | + | + | − | − | − | − |
|  | 0.001 | + | + | + | + | + | + |
| B. cereus | 0.1 | − | − | − | − | − | − |
|  | 0.05 | + | − | − | − | − | − |
|  | 0.01 | + | + | + | + | + | + |
|  | 0.005 | + | + | + | + | + | + |
|  | 0.001 | + | + | + | + | + | + |
| B. subtilis | 0.1 | − | − | − | − | − | − |
|  | 0.05 | − | − | − | − | − | − |

-continued

| Test Strain | Preparation of Example 4 | | | | | | |
|---|---|---|---|---|---|---|---|
| | Concentration of effective substance - % ES | Time to become effective/min. | | | | | |
| | | 1 | 2 | 5 | 10 | 20 | 30 |
| | 0.01 | + | + | + | + | + | + |
| | 0.005 | + | + | + | + | + | + |
| | 0.001 | + | + | + | + | + | + |

(C) Derivatives of an amine mixture composed of

60–70% by weight of $H_2N$—$CH_2CH_2$—$NH$—$CH_2CH_2CH_2$—$NH_2$ and

30–40% by weight of $H_2N$—$CH_2CH_2CH_2$—$NH$—$CH_2CH_2$—$NH$—$CH_2CH_2CH_2$—$NH_2$

EXAMPLE 5

Reaction product of the amine mixture with n-octyl chloride in a molar ratio of 1:3. 1 mole of the amine mixture is heated together with 4.8 moles of sodium hydroxide to 120° C. 3 moles of n-octyl chloride are slowly added to this mixture while stirring, and the reaction is allowed to continue for 15 hours at 135°–140° C. Thereupon, the reaction mixture is filtered hot, the inorganic residue is eliminated, and the filtrate of 490 g is used for preparing microbiocidal substances.

Analyses: Measured: in % by weight: C = 74.0; H = 14.1; N = 10.8.

10 parts of the reaction product are stirred together with 10 parts by weight of an adduct of 10 moles of ethylene oxide to 1 mole of i-tridecyl alcohol, with 75 parts of water and 5 parts of acetic acid until a clear solution allowing dilution in water is obtained. The pH value of this preparation was adjusted to 6.75 by means of acetic acid.

| Test Strain | Preparation of Example 5 | | | | | | |
|---|---|---|---|---|---|---|---|
| | Concentration of effective substance - % ES | Time to become effective/min. | | | | | |
| | | 1 | 2 | 5 | 10 | 20 | 30 |
| S. aureus | 0.1 | − | − | − | − | − | − |
| | 0.05 | − | − | − | − | − | − |
| | 0.01 | − | − | − | − | − | − |
| | 0.005 | + | − | − | − | − | − |
| | 0.001 | + | + | + | − | − | − |
| E. coli | 0.1 | − | − | − | − | − | − |
| | 0.05 | − | − | − | − | − | − |
| | 0.01 | − | − | − | − | − | − |
| | 0.005 | − | − | − | − | − | − |
| | 0.001 | + | + | + | + | − | − |
| P. vulgaris | 0.1 | − | − | − | − | − | − |
| | 0.05 | − | − | − | − | − | − |
| | 0.01 | + | + | + | + | + | + |
| | 0.005 | + | + | + | + | + | + |
| | 0.001 | + | + | + | + | + | + |
| P. aeruginosa | 0.1 | − | − | − | − | − | − |
| | 0.05 | − | − | − | − | − | − |
| | 0.01 | + | − | − | − | − | − |
| | 0.005 | + | + | + | + | + | + |
| | 0.001 | + | + | + | + | + | + |
| Candida albicans | 0.1 | − | − | − | − | − | − |
| | 0.05 | − | − | − | − | − | − |
| | 0.01 | − | − | − | − | − | − |
| | 0.005 | − | − | − | − | − | − |
| | 0.001 | + | + | − | − | − | − |
| Hansenula anomala | 0.1 | − | − | − | − | − | − |
| | 0.05 | − | − | − | − | − | − |
| | 0.01 | − | − | − | − | − | − |
| | 0.005 | + | − | − | − | − | − |
| | 0.001 | + | + | − | − | − | − |
| Geotrichum canadidum | 0.1 | − | − | − | − | − | − |
| | 0.05 | − | − | − | − | − | − |
| | 0.01 | − | − | − | − | − | − |
| | 0.005 | − | − | − | − | − | − |
| | 0.001 | + | + | − | − | − | − |
| Penicillium expansum | 0.1 | − | − | − | − | − | − |
| | 0.05 | − | − | − | − | − | − |
| | 0.01 | + | + | − | − | − | − |
| | 0.005 | + | + | + | + | − | − |

-continued

| Test Strain | Preparation of Example 5 | | | | | | |
|---|---|---|---|---|---|---|---|
| | Concentration of effective substance - % ES | Time to become effective/min. | | | | | |
| | | 1 | 2 | 5 | 10 | 20 | 30 |
| | 0.001 | + | + | + | + | + | − |
| Trichophyton mentagrophytes | 0.1 | − | − | − | − | − | − |
| | 0.05 | − | − | − | − | − | − |
| | 0.01 | − | − | − | − | − | − |
| | 0.005 | + | − | − | − | − | − |
| | 0.001 | + | + | + | − | − | − |
| Mikrosporum gypseum | 0.1 | − | − | − | − | − | − |
| | 0.05 | − | − | − | − | − | − |
| | 0.01 | − | − | − | − | − | − |
| | 0.005 | + | − | − | − | − | − |
| | 0.001 | + | + | + | − | − | − |
| B. cereus (spores) | 0.1 | − | − | − | − | − | − |
| | 0.05 | − | − | − | − | − | − |
| | 0.01 | + | + | + | + | − | − |
| | 0.005 | + | + | + | + | + | + |
| | 0.001 | + | + | + | + | + | + |
| B. substilis (spores) | 0.1 | − | − | − | − | − | − |
| | 0.05 | − | − | − | − | − | − |
| | 0.01 | + | + | + | + | − | − |
| | 0.005 | + | + | + | + | + | + |
| | 0.001 | + | + | + | + | + | + |

EXAMPLE 6

Reaction product of the amine mixture with n-dodecyl chloride in a molar ratio of 4:1. 16 moles of the amine mixture and 100 ml of water were heated to 120° C. 4 moles of n-dodecyl chloride are added in three portions to the above mixture and the reaction is allowed to proceed for 10 hours at 120°–130° C. Thereupon, 6.4 moles of sodium hydroxide are added in small quantities to the reaction mixture and the reaction is again allowed to proceed for 10 minutes at 130° C., whereupon the inorganic residue is removed by filtration. The filtrate is freed of non-converted $N_3/N_4$ amine mixture by distillation. The yield is 1,010 g of alkyl-polyamine mixture.

10 parts by weight of the product so prepared are stirred together with 10 parts by weight of an adduct of 10 moles of ethylene oxide to 1 mole of i-tridecyl alcohol, with 10 parts by weight of acetic acid and 70 parts by weight of water until a homogeneous solution is obtained. The pH value of the preparation was adjusted to 4.65 by means of acetic acid.

| Test Strain | Preparation of Example 6 | | | | | | |
|---|---|---|---|---|---|---|---|
| | Concentration of effective substance - % ES | Time to becomes effective/min. | | | | | |
| | | 1 | 2 | 5 | 10 | 20 | 30 |
| S. aureus | 0.1 | − | − | − | − | − | − |
| | 0.05 | − | − | − | − | − | − |
| | 0.01 | + | − | − | − | − | − |
| | 0.005 | + | − | − | − | − | − |
| | 0.001 | + | + | − | − | − | − |
| E. coli | 0.1 | − | − | − | − | − | − |
| | 0.05 | − | − | − | − | − | − |
| | 0.01 | − | − | − | − | − | − |
| | 0.005 | + | − | − | − | − | − |
| | 0.001 | + | + | + | − | − | − |
| P. vulgaris | 0.1 | + | + | − | − | − | − |
| | 0.05 | + | + | − | − | − | − |
| | 0.01 | + | + | − | − | − | − |
| | 0.005 | + | + | + | − | − | − |
| | 0.001 | + | + | + | + | + | + |
| P. aeruginosa | 0.1 | − | − | − | − | − | − |
| | 0.05 | − | − | − | − | − | − |
| | 0.01 | − | − | − | − | − | − |
| | 0.005 | + | − | − | − | − | − |
| | 0.001 | + | + | + | + | + | + |
| B. cereus (spores) | 0.1 | − | − | − | − | − | − |
| | 0.05 | − | − | − | − | − | − |
| | 0.01 | + | + | − | − | − | − |
| | 0.005 | + | + | + | + | + | − |
| | 0.001 | + | + | + | + | + | + |
| B. subtilis (spores) | 0.1 | − | − | − | − | − | − |
| | 0.05 | − | − | − | − | − | − |

-continued

| | Preparation of Example 6 | | | | | | |
|---|---|---|---|---|---|---|---|
| | Concentration of effective sub- | Time to becomes effective/min. | | | | | |
| Test Strain | stance - % ES | 1 | 2 | 5 | 10 | 20 | 30 |
| | 0.01 | + | + | + | − | − | − |
| | 0.005 | + | + | + | + | + | + |
| | 0.001 | + | + | + | + | + | + |

(D) Comparison Tests

The comparison tests were carried out using the compounds of German Pat. No. 2,049,399, preparation A and the compounds of German Pat. No. 2,113,208, preparation B. The results relating to the effectiveness of the sporicidal preparation of Example 1 were again used for comparison. Except for the effective subtances, the preparations in each case were identical and were adjusted to a pH value of 7.05.

| | Concentration of effective substance | Preparation A Time to act/min. | | | | | | Preparation B Time to act/min. | | | | | | Preparation of Example 1 Time to act/min. | | | | | |
|---|---|---|---|---|---|---|---|---|---|---|---|---|---|---|---|---|---|---|---|
| Test Strain | % ES | 1 | 2 | 5 | 10 | 20 | 30 | 1 | 2 | 5 | 10 | 20 | 30 | 1 | 2 | 5 | 10 | 20 | 30 |
| *B. cereus* (spores) | 0.1 | + | + | + | + | − | − | + | + | + | + | + | + | − | − | − | − | − | − |
| | 0.05 | + | + | + | + | + | − | + | + | + | + | + | + | − | − | − | − | − | − |
| | 0.01 | + | + | + | + | + | + | + | + | + | + | + | + | + | + | + | + | + | − |
| | 0.005 | + | + | + | + | + | + | + | + | + | + | + | + | + | + | + | + | + | + |
| | 0.001 | + | + | + | + | + | + | + | + | + | + | + | + | + | + | + | + | + | + |
| *B. subtilis* | 0.1 | + | + | + | + | + | − | + | + | + | + | + | + | − | − | − | − | − | − |
| | 0.05 | + | + | + | + | + | + | + | + | + | + | + | + | − | − | − | − | − | − |
| | 0.01 | + | + | + | + | + | + | + | + | + | + | + | + | + | + | + | + | + | + |
| | 0.005 | + | + | + | + | + | + | + | + | + | + | + | + | + | + | + | + | + | + |
| | 0.001 | + | + | + | + | + | + | + | + | + | + | + | + | + | + | + | + | + | + |

The values shown above deviate from the values listed in German Pat. No. 2,049,399. In order to carry out the comparison tests rationally and critically, spores from the same bacteria but of more resistant strains were selected.

It will be obvious to those skilled in the art that many modifications may be made within the scope of the present invention without departing from the spirit thereof, and the invention includes all such modifications.

What is claimed is:

1. A compound or mixture of compounds having the general formula

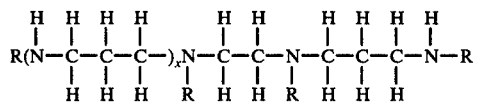

in which R is hydrogen or an alkyl group containing 8 to 18 carbon atoms, at least one R being alkyl, and $x$ is 0 or 1.

2. A compound according to claim 1 which is tri-n-octyl-N,N'-bis-(3-aminopropyl)-ethylenediamine.

3. A compound according to claim 1 which is N-(3-laurylaminopropyl)-N'-(3-aminopropyl)-ethylenediamine.

4. A process for killing microbes which comprises contacting said microbes with a microbiocidally effective amount of a compound or mixture of compounds having the formula

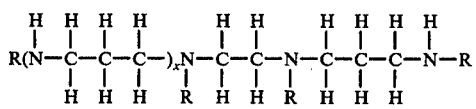

in which R is hydrogen or an alkyl group containing 8 to 18 carbon atoms, at least one R being alkyl, and $x$ is 0 or 1.

5. A process according to claim 4 in which the compound is tri-n-octyl-N,N'-bis-(3-aminopropyl)-ethylenediamine.

6. A process according to claim 4 in which the compound is N-(3-laurylaminopropyl)-N'-(3-aminopropyl)-ethylenediamine.

7. A microbiocidal composition comprising a carrier and a microbiocidally effective amount of a compound or mixture of compounds having the formula

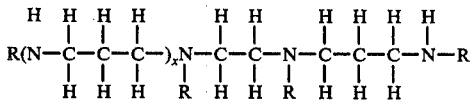

in which R is hydrogen or an alkyl group containing 8 to 18 carbon atoms, at least one R being alkyl, and $x$ is 0 or 1.

8. A microbiocidal composition according to claim 7 in which the compound is tri-n-octyl-N,N'-bis-(3-aminopropyl)-ethylenediamine.

9. A microbiocidal composition according to claim 7 in which the compound is N-(3-laurylaminopropyl)-N'-(3-aminopropyl)-ethylenediamine.

* * * * *